(12) United States Patent
Richard et al.

(10) Patent No.: US 9,447,123 B2
(45) Date of Patent: Sep. 20, 2016

(54) PROCESS FOR PREPARING 2-HYDROXYPHENYL ALKENYL BENZOTRIAZOLE COMPOUNDS; USE OF THE SAID COMPOUNDS OBTAINED VIA THE PROCESS IN THE SYNTHESIS OF SILOXANE COMPOUNDS CONTAINING A 2-HYDROXYPHENYLBENZOTRIAZOLE FUNCTION

(75) Inventors: Herve Richard, Gagny (FR); Jinzhu Xu, Paris (FR); Patricio Guerreiro, Avilly Saint Leonard (FR); Yuan Wang, Shanghai (CN); Jianping Guo, Jiangxi (CN)

(73) Assignee: L'OREAL, Paris (FR)

( * ) Notice: Subject to any disclaimer, the term of this patent is extended or adjusted under 35 U.S.C. 154(b) by 382 days.

(21) Appl. No.: 13/814,539

(22) PCT Filed: Oct. 25, 2010

(86) PCT No.: PCT/CN2010/001670
§ 371 (c)(1),
(2), (4) Date: Mar. 27, 2013

(87) PCT Pub. No.: WO2012/055063
PCT Pub. Date: May 3, 2012

(65) Prior Publication Data
US 2013/0231488 A1    Sep. 5, 2013

(51) Int. Cl.
*C07F 7/08* (2006.01)
*C07D 249/20* (2006.01)

(52) U.S. Cl.
CPC ........... *C07F 7/0879* (2013.01); *C07D 249/20* (2013.01); *C07F 7/0849* (2013.01)

(58) Field of Classification Search
CPC ... C07F 7/0849; C07F 7/0879; C07D 279/20
See application file for complete search history.

(56) References Cited

U.S. PATENT DOCUMENTS

| | | | |
|---|---|---|---|
| 5,089,250 A * | 2/1992 | Forestier et al. | ............... 424/43 |
| 5,254,542 A | 10/1993 | Sakuta et al. | |
| 5,618,520 A | 4/1997 | Hansenne et al. | |
| 6,864,325 B2 | 3/2005 | Zedda et al. | |
| 7,173,128 B2 | 2/2007 | Ravichandran et al. | |
| 7,244,776 B2 | 7/2007 | Ravichandran et al. | |
| 7,821,272 B2 | 10/2010 | Scholz et al. | |
| 2009/0270632 A1 | 10/2009 | Lu et al. | |

FOREIGN PATENT DOCUMENTS

| | | |
|---|---|---|
| GB | 2 077 747 A | 12/1981 |
| JP | 8 311046 | 11/1996 |
| JP | 10 212469 | 8/1998 |
| WO | 01 62821 | 8/2001 |
| WO | 03 016292 | 2/2003 |
| WO | 2008 131921 | 11/2008 |

OTHER PUBLICATIONS

Carey et al. "Advanced Organic Chemistry, Fourth Edition, Part A: Structure and Mechanisms" 2000, Kluwer Academic/Plenum Publishers, p. 632.*
U.S. Appl. No. 13/814,592, filed Feb. 6, 2013, Richard, et al.
International Search Report Issued Aug. 11, 2011 in PCT/CN10/01670 Filed Oct. 25, 2010.
Extended Search Report issued Mar. 21, 2014 in European Patent Application No. 10858792.4.

* cited by examiner

*Primary Examiner* — Joseph Kosack
(74) *Attorney, Agent, or Firm* — Oblon, McClelland, Maier & Neustadt, L.L.P.

(57) ABSTRACT

The process for preparing 2-hydroxyphenyl alkenyl benzotriazole compounds and the process for preparing siloxane compounds containing 2-hydroxyphenyl benzotriazole function are disclosed.

18 Claims, No Drawings

PROCESS FOR PREPARING 2-HYDROXYPHENYL ALKENYL BENZOTRIAZOLE COMPOUNDS; USE OF THE SAID COMPOUNDS OBTAINED VIA THE PROCESS IN THE SYNTHESIS OF SILOXANE COMPOUNDS CONTAINING A 2-HYDROXYPHENYLBENZOTRIAZOLE FUNCTION

CROSS-REFERENCE TO RELATED APPLICATIONS

This application is a National Stage of PCT/CN2010/001670 filed Oct. 25, 2010.

The present invention relates to a process for preparing a 2-hydroxyphenyl alkenyl benzotriazole compound in particular of formula (1) that will be defined in detail later.

The present invention relates to a process for preparing siloxane compounds containing a 2-hydroxyphenylbenzotriazole function in particular of formula (3) that will be defined in detail later, comprising a) the preparation of a 2-hydroxyphenyl alkenyl benzotriazole compound obtained according to the preceding preparation process, and b) the hydrosilylation reaction with the said 2-hydroxyphenyl alkenyl benzotriazole compound with a siloxane containing an SiH function, in the presence of a suitable catalyst and a suitable solvent.

It is known that light radiation with wavelengths of between 280 nm and 400 nm allows browning of the human epidermis, and that rays with wavelengths more particularly of between 280 and 320 nm, which are known as UV-B rays, may harm the development of a natural tan. For these reasons, and also for aesthetic reasons, there is constant demand for means for controlling this natural tanning in order thus to control the colour of the skin; this UV-B radiation should thus be screened out.

It is also known that UV-A rays, with wavelengths of between 320 and 400 nm, which cause browning of the skin, are liable to induce impairment thereof, especially in the case of sensitive skin or of skin that is continually exposed to sunlight. UV-A rays in particular cause loss of elasticity of the skin and the appearance of wrinkles, leading to premature ageing of the skin. Thus, for aesthetic and cosmetic reasons, for instance maintenance of the natural elasticity of the skin, more and more people wish to control the effect of UV-A rays on their skin. It is thus desirable also to screen out UV-A radiation.

For the purpose of protecting the skin and keratin materials against UV radiation, antisun compositions comprising organic or inorganic screening agents that are active in the UV-A range and active in the UV-B range are generally used.

Many sectors of non-cosmetic industry also resort to the use of UV-screening agents for photoprotecting various materials against the effects of UV radiation and in particular sunlight.

This is especially the case for paint, ink or protective covering formulations intended to be applied onto products that are permanently exposed to UV radiation such as building materials, the materials used in the motor vehicle industry, and packaging plastics. UV-screening agents that are transparent, photostable, compatible with the usual ingredients contained in the said formulations and effective in the light-fastness of the desired colour are most particularly sought for these colouring formulations.

This is also the case for the polymer compositions used especially in the manufacture of plastics that are stable on storage, in which UV-screening agents are sought that are particularly suited to processes for manufacturing and transforming polymers that especially need to have good resistance to high temperatures for extrusion.

In the industry of textiles made from natural fibres, artificial fibres or synthetic fibres, broad-spectrum photostable UV-screening agents are sought that are compatible with the processes for manufacturing the said fibres, especially in the context of manufacturing polyamide fibres such as nylon, which are resistant to strong heat and which allow incorporation of UV protection during extrusion. UV-screening agents that show good affinity for and good adhesion to the fibres, thus affording them in particular good resistance to successive washing, are also sought. The desired UV-screening agents should also allow good protection not only of textile fibres but also of the skin and of the other human is keratin materials in contact with the said fibres.

Similar problems also arise in the manufacture of paper generally made of cellulose fibres, in which the UV-screening agents used must also be photostable, transparent and compatible with the other usual ingredients and adapted to the various papermaking techniques.

The industry of mineral or organic glasses and especially of those used in ophthalmology is in search of UV-screening agents that must have a broad spectrum of action (active in the UV-A range and in the UV-B range), which are photostable, transparent and compatible with the various techniques for treating glasses, for instance the process for attaching glass to the matrix or the application of a photoprotective covering, for example in the case of polycarbonate glasses.

One particularly interesting family of organic screening agents with absorbent properties both in the UV-A range and in the UV-B range is that of siloxane compounds containing a 2-hydroxyphenylbenzotriazole function.

The term "siloxane compound containing a 2-hydroxybenzotriazole function" means any molecule comprising in its structure at least one —SiO group and at least one 2-hydroxyphenylbenzotriazole group; the said molecule possibly being in the form of a simple siloxane or alkoxysilane compound, an oligosiloxane or a polysiloxane.

In particular, siloxane compounds containing a 2-hydroxyphenylbenzotriazole function of formula (4) below:

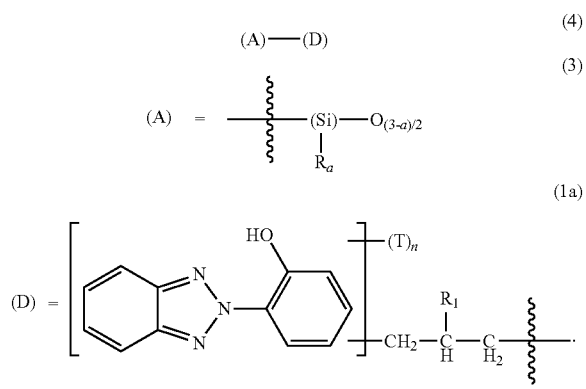

in which group (A) represents the silicone part of formula (4) with:

R, which may be identical or different, denote a linear or branched and optionally halogenated or unsaturated $C_1$-$C_{30}$ alkyl radical, a $C_6$-$C_{12}$ aryl radical, a linear or branched $C_1$-$C_{10}$ alkoxy radical or a group —OSi(CH$_3$)$_3$;

a is an integer between 0 and 2 inclusive;

and in which group (D) represents the group of formula (1a) with:

n is an integer between 0 and 3 inclusive;

T, which may be identical or different, are chosen from linear or branched $C_1$-$C_8$ alkyl radicals, halogens, preferably chlorine, and linear or branched $C_1$-$C_4$ alkoxy radicals;

$R_1$ represents hydrogen or a methyl radical, are known.

In addition to the units of formula (A), the organosiloxane may comprise units of formula:

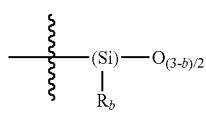

in which,

R has the same meaning as in formula (3);

b=1, 2 or 3.

Preferably, the compounds of formula (4) are represented by formulae (3a) or (3b) below:

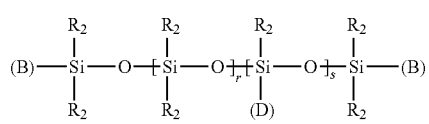
(3a)

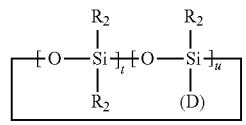
(3b)

in which:

(D) corresponds to formula (1a) as defined above, $R_2$, which may be identical or different, are chosen from linear or branched $C_1$-$C_{20}$ alkyl, phenyl, 3,3,3-trifluoropropyl and trimethylsilyloxy radicals or the hydroxyl radical, (B), which may be identical or different, are chosen from the radicals $R_2$ and the group (D), r is an integer between 0 and 200 inclusive, s is an integer ranging from 0 to 50 and if s=0, at least one of the two symbols (B) denotes (D), u is an integer ranging from 1 to 10, t is an integer ranging from 0 to 10, it being understood that t+u is greater than or equal to 3.

The linear or cyclic diorganosiloxanes of formula (3a) or (3b) are random oligomers or polymers in which $R_2$ is preferably a methyl radical.

The linear diorganosiloxanes of formula (3a) are particularly preferred.

As examples of compounds of formula (3) that are particularly preferred, mention will be made of the compounds of formulae (a) to (h) below:

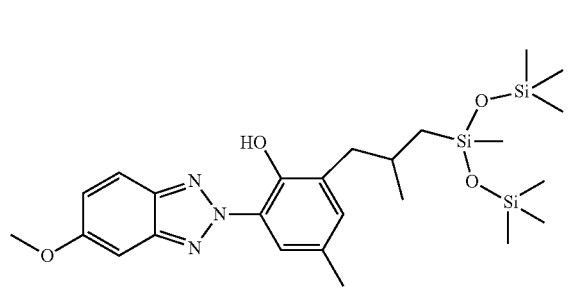
(a)

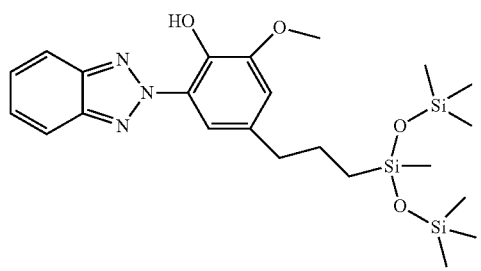
(b)

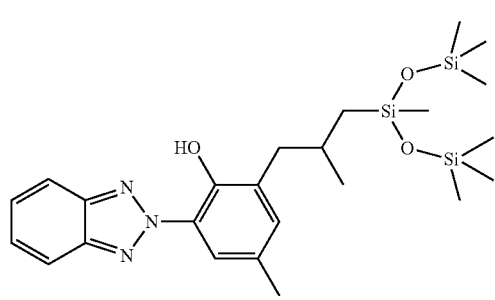
(c)

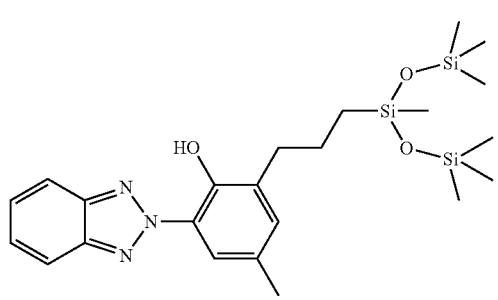
(d)

-continued

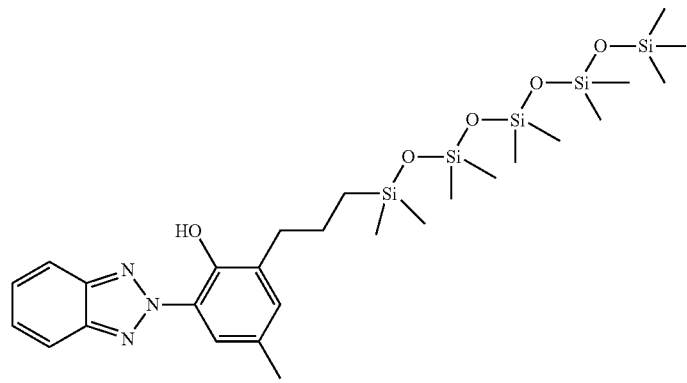
(e)

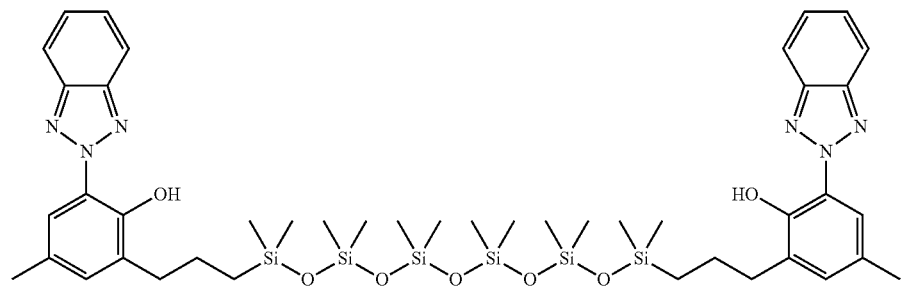
(f)

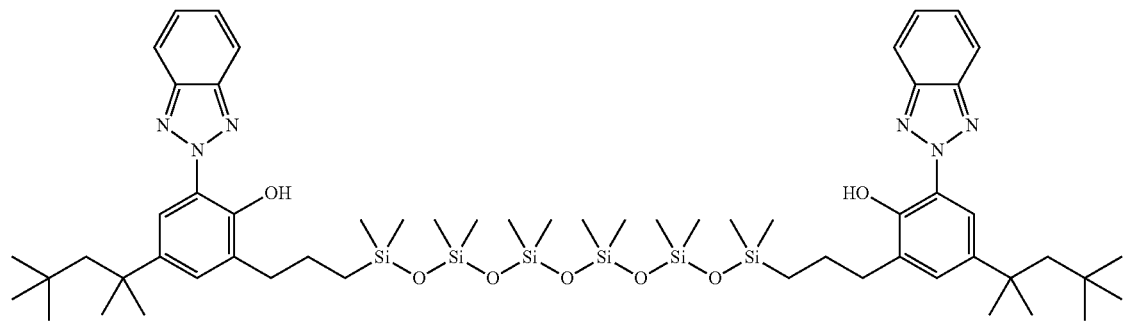
(g)

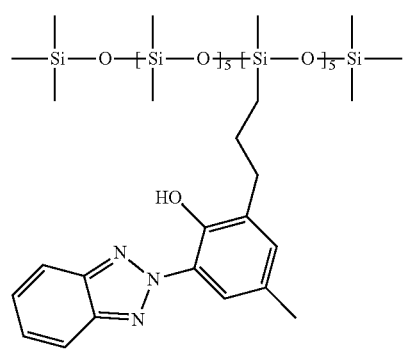
(h)

random derivative r = s = 5

(a)=2-(5-methoxy-2H-1,2,3-benzotriazol-2-yl)-4-methyl-6-(2-methyl-3-{1,3,3,3-tetramethyl-1-[(trimethylsilyl)oxy]disiloxanyl}propyl)phenol (b) 2-(2H-1,2,3-benzotriazol-2-yl)-6-methoxy-4-(3-{1,3,3,3-tetramethyl-1-[(trimethylsilyl)oxy]disiloxanyl}propyl)phenol (c)=2-(2H-1,2,3-benzotriazol-2-yl)-4-methyl-6-(2-methyl-3-{1,3,3,3-tetramethyl-1-[(trimethylsilyl)oxy]disiloxanyl}propyl)phenol (d)=2-(2H-1,2,3-benzotriazol-2-yl)-4-methyl-6-(3-{1,3,3,3-tetramethyl-1-[(trimethylsilyl)oxy]disiloxanyl}propyl)phenol (e)=2-(2H-1,2,3-benzotriazol-2-yl)-4-methyl-6-[-3-(undecamethylpentasiloxanyl)propyl]phenol (f)=2-(2H-1,2,3-benzotriazol-2-yl)-6-[3-(11-{3-[3-(2H-1,2,3-benzotriazol-2-yl)-2-hydroxy-5-methylphenyl]propyl}-1,1,3,3,5,5,7,7,9,9,11,11-dodecamethylhexasiloxanyl)propyl]-4-methylphenol (g) 2-(2H-1,2,3-benzotriazol-2-yl)-6-[3-(11-{3-[3-(2H-1,2,3-benzotriazol-2-yl)-2-hydroxy-5-(1,1,3,3-tetramethylbutyl)phenyl]propyl}-1,1,3,3,5,5,7,7,9,9,11,11-dodecamethylhexasiloxanyl)propyl]-4-(1,1,3,3-tetramethylbutyl)phenol .Even more particularly preferred are the derivatives of formula (3a) in which r=0, s=1, and $R_2$ and (B) are methyl.

Even more preferably, the compound Drometrizole Trisiloxane (CTFA name) is known, corresponding to the following formula:

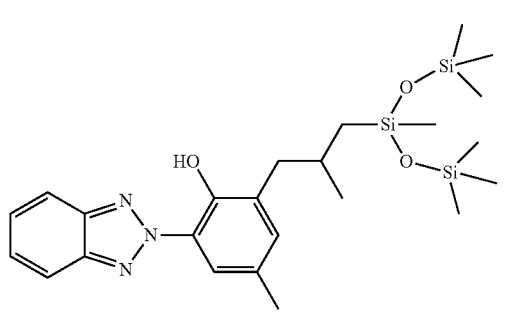

(c)

product manufactured by the company Rhodia under the trade name Silatrizole.

These compounds and their syntheses have been described in patents U.S. Pat. Nos. 4,316,033, 4,373,060, EP 0 388 218, U.S. Pat. No. 5,089,250, EP 0 354 145, EP 0 708 108, EP 0 711 779 and patent application WO 94/06404.

The siloxane compounds containing a 2-hydroxyphenylbenzotriazole function and especially those of formula (4) are obtained, according to these documents, by hydrosilylation reaction of a 2-hydroxyphenyl alkenyl benzotriazole compound (especially that of formula (1) defined below) with a siloxane containing an SiH function (especially of formula (2) defined below) in the presence of a suitable catalyst and a suitable solvent (in particular toluene) and according to the reaction scheme A below:

SCHEME A

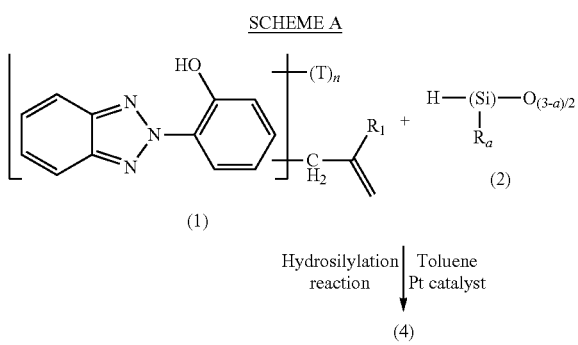

In formula (1), T, n and $R_1$ have the same meaning as in the preceding formula (1a), and in formula (2), R and a have the same meaning as in the preceding formula (3).

As emerges from formula (1a) given above, the attachment of the chain unit:

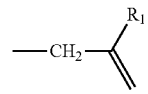

to the 2-hydroxyphenylbenzotriazole unit, which thus ensures attachment of the said 2-hydroxyphenylbenzotriazole unit to the silicon atom of the silicone chain, takes place exclusively in position 3 (aromatic nucleus bearing the hydroxyl function) or in position 5 (when position 3 contains a radical T).

Similarly, the attachment of the substituent unit T may take place in all the other positions available on the 2-hydroxyphenylbenzotriazole. However, preferably, this attachment takes place in position 3, 4, 4', 5 and/or 6.

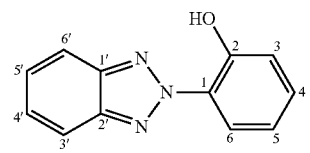 [SMILES: Oc1ccccc1-n1nc2ccccc2n1]

The 2-hydroxyphenyl alkenyl benzotriazole compounds, starting products in the synthesis of the siloxane screening agents containing a 2-hydroxyphenylbenzotriazole function, are known per se and their syntheses have been described in patents FR 1 325 404, U.S. Pat. Nos. 4,316,033, 4,328,346, 4,373,060, GB 2 077 280, EP 0 392 883, EP 0 708 108, EP 0 711 779 and U.S. 2009/0 270 632.

In patent FR 1 325 404, the 2-hydroxyphenyl alkenyl benzotriazole compounds are obtained via a Claisen rearrangement on a 2-O-alkenylphenylbenzotriazole compound, according to the following operating conditions: without solvent, or alternatively with dimethylaniline or specific polymers as solvents (commercial polyethylene glycol terephthalate), at 180-220° C. and recrystallization in alcohol. The overall yields for this process are unsatisfactory.

In patents U.S. Pat. Nos. 4,316,033, 4,373,060 and GB 2 077 280, the 2-hydroxyphenyl alkenyl benzotriazole compounds are obtained via a synthetic process comprising two chemical steps. In a first stage, alkylation of a 2-hydroxy-5-alkylphenylbenzotriazole compound is performed with an alkenyl halide in the presence of a base (for example potassium carbonate or sodium methoxide) and with, as solvent: acetone, diethyl ketone or 2-butanone. The product resulting from this alkylation is heated at 200° C. under a nitrogen atmosphere for 1 hour 30 minutes to give, after recrystallization from a methanol/chloroform mixture, the corresponding 2-hydroxyphenyl alkenyl benzotriazole derivative. The overall yield for the two steps (44%) of this process is unsatisfactory.

In patent EP 0 392 883, the 2-hydroxyphenyl alkenyl benzotriazole derivatives are also obtained via a synthetic process in two chemical steps. In the first step, an alkenyl halide is reacted with a 2-hydroxyphenyl-5-alkylbenzotriazole compound in the presence of a base (an alkali metal or alkaline-earth metal hydroxide or carbonate, or an alkali metal amide, alkoxide or hydride) in a solvent such as water or an organic solvent such as an alcohol, dioxane, dimethyl sulfoxide or dimethylformamide, at a temperature between room temperature and the boiling point of the solvent. The Claisen rearrangement is performed on the product resulting from the first step by heating to at least 170° C. approximately, optionally in the presence of a solvent. The overall yield for the two steps of this process is not entirely satisfactory.

In patent application U.S. 2009/0 270 632, the 2-hydroxyalkenylphenyl-benzotriazole compounds are also obtained via a synthetic process comprising the following steps:
(a) a 2-hydroxy-5-alkylphenylbenzotriazole compound, a base (sodium carbonate, potassium carbonate, sodium hydrogen carbonate, potassium hydrogen carbonate, triethylamine or tricaprylylamine) and molecular sieves (3 Å and 5 Å calcium aluminium silicate) in a first solvent (N,N-dialkylaniline containing from 1 to 3 carbon atoms) and 3-chloro-2-alkylpropylene dissolved in a second solvent (an alkyl ketone containing from 1 to 5 carbon atoms) are mixed together; the ratio of benzotriazole derivative to base being between 1/0.1 and 1/1;
(b) the various solutions are mixed together in the reactor;
(c) the reactor is made inert with nitrogen;
(d) the reaction medium is heated to a reaction temperature of between 70° C. and 190° C.;
(e) the resulting mixture is filtered;
(f) the product is recrystallized (from halogenated solvents, N,N-dimethyl-formamide, non-aromatic alcohol or halobenzene). Although the overall yields for the given examples are between 72% and 86%, there is still a need to improve this yield. Furthermore, the solvents N,N-dimethylformamide, N,N-dialkylaniline and the amines triethylamine and tricaprylylamine used in this process are products that are known for their toxic effects and their environmental unfriendliness.

There is still a need to find a process for preparing a 2-hydroxyphenyl alkenyl benzotriazole compound with a better overall yield, without the drawbacks encountered in the prior art processes.

The Applicant has discovered, surprisingly, that this objective can be achieved with a process for preparing a 2-hydroxyphenyl alkenyl benzotriazole compound, characterized in that it comprises at least the following two chemical steps:
1) an etherification is performed on a 2-hydroxyphenylbenzotriazole compound in water and/or at least one suitable organic solvent by reacting an alkenyl halide in the presence of at least one phase-transfer agent and of at least one base so as to obtain the corresponding 2-O-alkenylphenylbenzotriazole compound;
2) a Claisen rearrangement is performed on the 2-O-alkenylphenylbenzotriazole compound thus obtained, by heating the reaction mixture to a temperature above 170° C. with at least one suitable organic solvent.

This process may be represented by Scheme B below:

SCHEME B

Ether formation

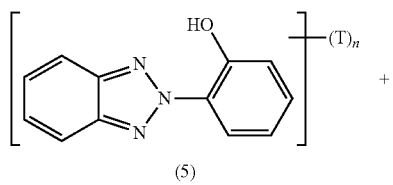

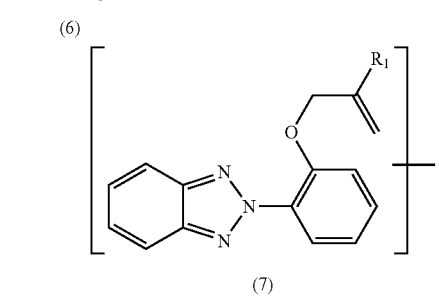

Claisen rearrangement

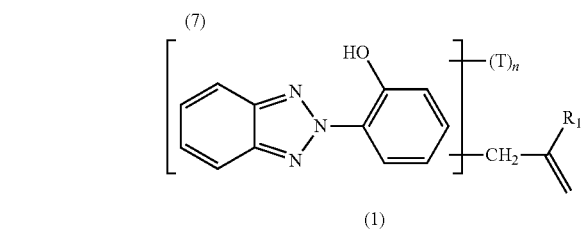

Such a process thus makes it possible to achieve overall yields of greater than 80% and purity levels of greater than 99% without the drawbacks mentioned previously. Furthermore, this process has the advantage of being able to be performed in a single reactor (one-pot).

This discovery forms the basis of the present invention.

The present invention thus relates to a process for preparing a 2-hydroxyphenyl alkenyl benzotriazole compound, characterized in that it comprises at least the following two chemical steps:
1) an etherification is performed on a 2-hydroxyphenylbenzotriazole compound in water and/or at least one suitable organic solvent by reacting an alkenyl halide in the presence of at least one phase-transfer agent and of at least one base so as to obtain the corresponding 2-O-alkenylphenylbenzotriazole compound of formula (7);
2) a Claisen rearrangement is performed on the 2-O-alkenylphenylbenzotriazole compound thus obtained, by heating the reaction mixture to a temperature above 170° C. with at least one suitable organic solvent.

The first chemical step of the process according to the invention is a standard etherification between an alkenyl halide of formula (6) and a 2-hydroxyphenyl-benzotriazole derivative of formula (5).

The second chemical step of the process according to the invention involves a Claisen rearrangement in which the alkenyl ether group migrates from the oxygen to the carbon ortho (or para) to the hydroxyl group under the conditions described by Tarbell (Organic Reactions, Vol. 2, John Wiley, New York, 1944, page 1) by heating the compound of formula (7) to at least 170° C. approximately.

For the etherification step, the temperatures of the reaction mixture are preferably between 20° C. and 150° C. and more particularly between 60° C. and 90° C.

For the Claisen rearrangement step, the temperatures of the reaction mixture are preferably between 170° C. and 250° C. and more particularly between 200° C. and 220° C.

More particularly, the process in accordance with the invention comprises the following steps:
i) an etherification is performed on a 2-hydroxyphenylbenzotriazole compound in water and/or at least one suitable organic solvent, by reacting an alkenyl halide in the presence of at least one phase-transfer agent and of at least one base so as to obtain the corresponding 2-O-alkenylphenylbenzotriazole compound of formula (7);
ii) the reaction mixture is cooled to room temperature and the reaction medium is preferably diluted with water and/or the said suitable organic solvent(s);
iii) total removal of the water from the reaction medium is performed;
iv) a Claisen rearrangement is performed on the 2-O-alkenylphenylbenzotriazole compound obtained in step i) by heating the reaction mixture to a temperature of greater than 170° C. in the presence of at least one suitable organic solvent;
v) the solvent(s) are eliminated;
vi) recrystallization is performed in the presence of at least one recrystallization solvent.

Preferentially, the process of the invention will be performed in a single reactor.

The present invention more particularly relates to a process for preparing a 2-hydroxyalkenylphenylbenzotriazole compound of formula (1) below:

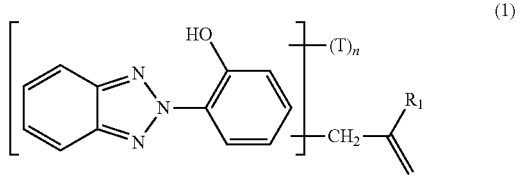

in which
n is an integer between 0 and 3 inclusive;
T, which may be identical or different, are chosen from linear or branched $C_1$-$C_8$ alkyl radicals, halogens and linear or branched $C_1$-$C_4$ alkoxy radicals;
$R_1$ represents hydrogen or a methyl radical,
characterized in that it comprises at least the following two chemical steps:
1) an etherification is performed on a compound of formula (5) below:

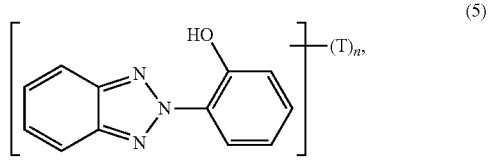

in which the radicals T and n have the same meanings indicated in formula (1) in water and/or at least one suitable organic solvent by reacting, in the presence of at least one phase-transfer agent and of at least one base, an alkenyl halide of formula (6) below:

in which X denotes a halogen atom, preferably bromine or chlorine, and $R_1$ denotes hydrogen or methyl, the said halide preferably being introduced by addition to the reaction medium;
2) a Claisen rearrangement is performed on the compound thus obtained of formula (7) below:

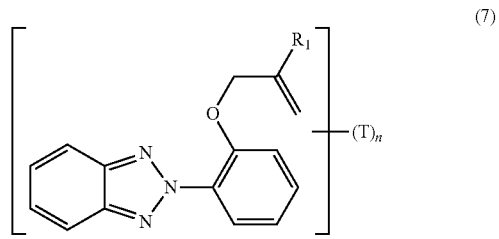

in which T, n and $R_1$ have the same meanings indicated in formula (1), by heating the reaction mixture to a temperature of greater than 170° C. in the presence of at least one suitable organic solvent.

According to one preferential form, the organic solvent(s) that may be used in the etherification step, optionally in step ii) of cooling the reaction medium and in the Claisen rearrangement step, are water-immiscible and have a boiling point of greater than 200° C., preferably between 200 and 270° C. and more preferentially between 200 and 220° C.

The term "water-immiscible solvent" means any solvent that forms with water a heterogeneous mixture with two separate phases.

Among the water-immiscible organic solvents with a boiling point of greater than 200° C., mention may be made of: benzyl alcohol (boiling point: 205° C.), diethylene glycol monobutyl ether (boiling point: 224-228° C.), diphenyl ether (boiling point: 258° C.), tetralin (boiling point: 206-208° C.), methylnaphthalene (boiling point: 244° C.) and the biphenyl/diphenyl ether mixture (boiling point: 257° C.). Benzyl alcohol will be more particularly preferred.

Among the 2-hydroxyphenylbenzotriazole derivatives of formula (5) that may be used as starting material in the process of the invention, mention may be made of the following compounds: 2-(2-hydroxy-5-methylphenyl)benzotriazole, 2-(2-hydroxy-5-tert-octylphenyl)benzotriazole, 2-(2'-hydroxy-5'-methylphenyl)-5-chlorobenzotriazole. 2-(2-Hydroxy-5-methylphenyl)benzotriazole will be preferred.

Among the alkenyl halides that may be used in the process of the invention, mention may be made of the following compounds: 1-chloro-2-propene (allyl chloride), 1-bromo-2-propene (allyl bromide), 1-chloro-2-methyl-2-propene (methallyl chloride) and 1-bromo-2-methyl-2-propene (methallyl bromide), in a ratio that may preferably range from 1.05 to 1.7 equivalents relative to the starting 2-hydroxyphenylbenzotriazole.

Methallyl chloride will be preferred. The preferential ratio will be between 1.3 and 1.5 equivalents relative to the starting 2-hydroxyphenylbenzotriazole compound.

The concentration of the starting 2-hydroxyphenylbenzotriazole derivative in the reaction medium of the etherification step preferably ranges from 5% to 80% by weight and preferentially from 20% to 50% by weight relative to the total weight of the reaction medium of the etherification step.

Among the phase-transfer agents that may be used in the process of the invention, mention may be made of the following compounds: tetrabutylammonium halides, tetrabutylammonium hydrogenosulfate, benzyltrimethylammonium chloride and preformed catalysts between tributylamine and the alkenyl halides. They will preferably be present in a ratio ranging from 3 mol % to 15 mol % relative to the starting 2-hydroxyphenylbenzotriazole derivative.

Tetrabutylammonium bromide and the preformed catalyst between tributylamine and methallyl chloride will be preferred. They will be used in a preferential ratio of between 3 mol % and 6 mol % relative to the starting 2-hydroxyphenylbenzotriazole.

Among the base that may be used in the process of the invention, mention may be made of the following compounds: alkali metal bases such as sodium bicarbonate, sodium carbonate, potassium bicarbonate, potassium carbonate, sodium hydroxide and potassium hydroxide. It is preferably used in a ratio ranging preferably from 0.7 to 1.5 equivalents relative to the starting 2-hydroxyphenylbenzotriazole of formula (5). Potassium bicarbonate will be preferred, in a preferential ratio of from 1.0 to 1.2 equivalents relative to the starting 2-hydroxyphenylbenzotriazole.

Among the recrystallization solvents, mention may be made of isopropanol, methanol, ethanol and benzyl alcohol, or mixtures thereof. Isopropyl alcohol will be preferred.

Another subject of the invention thus relates to a process for preparing a siloxane compound containing a benzotriazole function, characterized in that it comprises at least the following steps:
a) a 2-hydroxyphenyl alkenyl benzotriazole compound is prepared according to the process defined previously;
b) a hydrosilylation reaction is performed on the said 2-hydroxyphenyl alkenyl benzotriazole compound in the presence of a catalyst and of a suitable solvent with a siloxane containing an SiH function.

More particularly, the invention relates to a process for preparing a siloxane compound containing a benzotriazole function of formula (4) below:

$$(A)-(D) \quad (4)$$

$$(A) = -\!\!\left\{\!\!(Si)-O_{(3-b)/2}\right\}\!\!- \quad (3)$$
$$\phantom{(A) = }\quad R_a$$

$$(D) = \left[\begin{array}{c}\text{HO}\\ \text{benzotriazole-phenyl}\end{array}(T)_n\; -CH_2-\underset{H}{\overset{R_1}{C}}-\underset{H_2}{C}-\right] \quad (1a)$$

in which group (A) represents the silicone part of formula (3) with:
R, which may be identical or different, denote a linear or branched and optionally halogenated or unsaturated $C_1$-$C_{30}$ alkyl radical, a $C_6$-$C_{12}$ aryl radical, a linear or branched $C_1$-$C_{10}$ alkoxy radical or a group —OSi(CH$_3$)$_3$;
a is an integer between 0 and 2 inclusive;
and in which group (D) represents a group of formula (1a) with:
n is an integer between 0 and 3 inclusive;
T, which may be identical or different, are chosen from linear or branched $C_1$-$C_8$ alkyl radicals, halogens and linear or branched $C_1$-$C_4$ alkoxy radicals;
$R_1$ represents hydrogen or a methyl radical.

In addition to the units of formula (A), the organosiloxane may comprise units of formula:

$$-\!\!\left\{\!\!(Si)-O_{(3-b)/2}\right\}\!\!-$$
$$\phantom{xxxx}R_b$$

in which,
R has the same meaning as in formula (3);
b=1, 2 or 3.
characterized in that it comprises at least the following steps:
a) a 2-hydroxyphenyl alkenyl benzotriazole compound of formula (1) below is prepared:

$$\left[\begin{array}{c}\text{HO}\\ \text{benzotriazole-phenyl}\end{array}(T)_n\; -CH_2-\overset{R_1}{=}\right] \quad (1)$$

in which $R_1$, T and n have the same meaning as in formula (1a), according to the process as defined previously;
b) a hydrosilylation reaction is performed on the said 2-hydroxyphenyl alkenyl benzotriazole compound of formula (1) with a siloxane containing an SiH function of formula (2) below:

$$H-\!(Si)-O_{(3-a)/2} \quad (2)$$
$$\phantom{xxx}R_a$$

in which R and a have the same meaning as in formula (3), in the presence of a suitable catalyst and a suitable solvent.

Among 2-hydroxyphenyl benzotriazole derivatives of formula (1) that can be used as starting product in the process of the invention, mention may be made of the following derivatives of formulae (i) to (m):

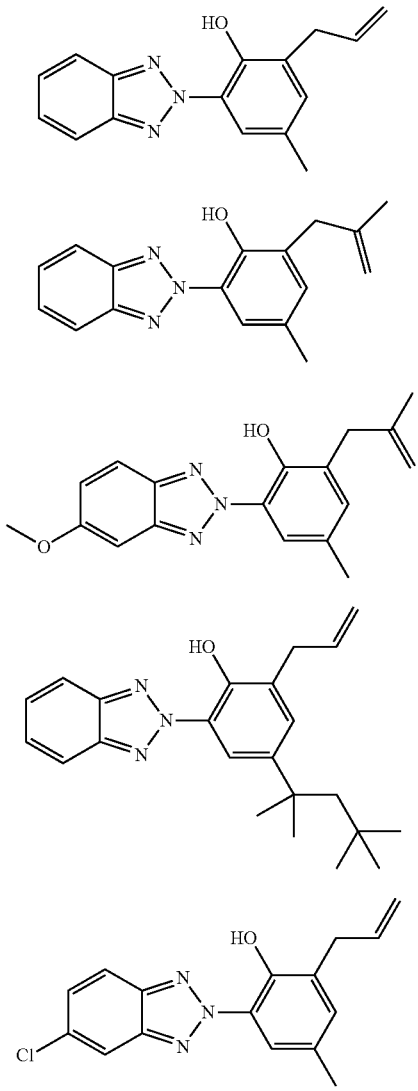

(i)=6-allyl-2-(2H-1,2,3-benzotriazol-2-yl)-4-methylphenol
(j)=2-(2H-1,2,3-benzotriazol-2-yl)-4-methyl-6-(2-methylprop-2-enyl)phenol;
(k)=2-(5-methoxy-2H-1,2,3-benzotriazol-2-yl)-4-methyl-6-(2-methylprop-2-enyl)phenol
(l)=6-allyl-2-(2H-1,2,3-benzotriazol-2-yl)-4-(t-octyl)phenol
(m)=2-(5-chloro-2H-1,2,3-benzotriazol-2-yl)-4-methyl-(6-allyl)phenol Even more preferably, use will be made of the compound 2-(2H-1,2,3-benzotriazol-2-yl)-4-methyl-6-(2-methylprop-2-enyl)phenol of formula (j) below:

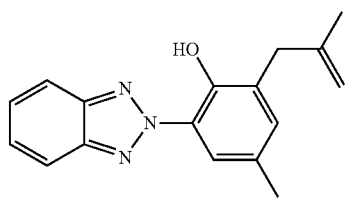

The siloxane of formula (2) that may be used according to the invention is preferentially chosen from 1,1,1,3,5,5,5-heptamethyltrisiloxane, diethoxy(methyl)silane and 1,1,1,5,5,5-hexamethyl-3-[(trimethylsilyl)oxy]trisiloxane. 1,1,1,3,5,5,5-Heptamethyltrisiloxane will be preferred.

The concentration of the siloxane of formula (2) in the reaction medium containing the 2-hydroxyalkenylphenylbenzotriazole compound of formula (1) may range between 30% and 90% and preferentially from 40% to 70%.

The siloxane of formula (2) used is placed in a ratio of 1.0 to 1.5 equivalents is relative to the 2-hydroxyphenylbenzotriazole derivative of formula (1), and more preferentially from 1.0 to 1.1 equivalents.

The catalysts used to perform the hydrosilylation reaction on the 2-hydroxyalkenylbenzotriazole compounds with the siloxanes containing an SiH function are fully described in the literature; mention may be made in particular of the complexes of platinum and of an organic product described in patents U.S. Pat. Nos. 3,159,601, 3,159,602, 3,220,972, EP 0 057 459, EP 10 188 978 and EP 0 190 530 and the complexes of platinum and of vinyl organopolysiloxanes described in patents U.S. Pat. Nos. 3,419,593, 3,377,432, 3,715,334 and 3,814,730 (Karstedt catalyst).

The solvent used for the hydrosilylation is preferably toluene.

More particularly, the invention relates to a process for preparing the compound Drometrizole Trisiloxane corresponding to the following formula:

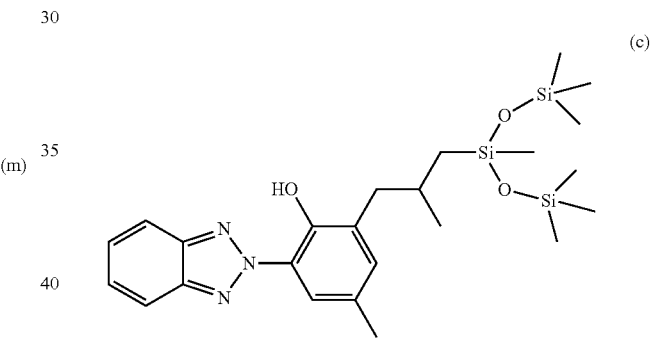

comprising at least the following steps:
a) the compound 2-(2H-1,2,3-benzotriazol-2-yl)-4-methyl-6-(2-methylprop-2-enyl)phenol is prepared according to the process as defined previously;
b) a hydrosilylation reaction is performed on the said compound with the siloxane containing an SiH function: 1,1,1,3,5,5,5-heptamethyltrisiloxane in the presence of a suitable catalyst and a suitable solvent.

Concrete but in no way limiting examples illustrating the invention will now be given.

EXAMPLE 1

Preparation of 2-(2H-1,2,3-benzotriazol-2-yl)-4-methyl-6-(2-methylprop-2-enyl)phenol in a Water/Benzyl Alcohol Two-Phase Mixture 2-(2-Hydroxy-5-methylphenyl)benzotriazole (2 g; 8.9 mmol) is charged under nitrogen into a reactor with potassium carbonate (1.83 g; 13.1 mmol), tetrabutylammonium bromide (143.1 mg; 0.44 mmol) and 10 ml of a water/benzyl alcohol mixture (4/1). The medium is heated to 80-85° C. and methallyl chloride (1.212 g; 13.4 mmol) is added dropwise. After addition, the medium is heated at 80-85° C.

After 17 hours, the medium is cooled and the phases are allowed to separate by settling. The organic phase is washed with water (twice 2 ml). The water is removed by distillation and the benzyl alcohol solution is used directly in reaction at 200° C. After reaction, the solvent is evaporated off and the crude product is taken up at 80° C. in 4.5 ml of isopropanol. The medium is then cooled to a temperature of between 0 and 10° C. The solid is filtered off and washed with cold isopropanol. After drying under vacuum, 2 g of white crystals are obtained (81% yield and 99.5% purity).

EXAMPLE 2

Preparation of 2-(2H-1,2,3-benzotriazol-2-yl)-4-methyl-6-(2-methylprop-2-enyl)phenol in Benzyl Alcohol Alone 2-(2-Hydroxy-5-methylphenyl)benzotriazole (2 g; 8.9 mmol) is charged under nitrogen into a reactor with potassium carbonate (1.83 g; 13.1 mmol), tetrabutylammonium bromide (114.5 mg; 0.35 mmol) and 8 ml of benzyl alcohol. The medium is heated to 80-85° C. and methallyl chloride (1.212 g; 13.4 mmol) is added dropwise. After addition, the medium is maintained at 80-85° C. After 18 hours, the medium is cooled and diluted with 2 ml of water. The aqueous phase is separated out and the organic phase is washed with water (twice 1 ml). The water is removed by distillation and the benzyl alcohol solution is used directly in reaction at 200° C. After reaction, the solvent is evaporated off and the crude product is taken up at 80° C. in 4.5 ml of isopropanol. The medium is then cooled to a temperature of between 0 and 10° C. The solid is filtered off and washed with cold isopropanol. After drying under vacuum, 2.1 g of white crystals are obtained (83% yield and 99.5% purity).

EXAMPLE 3

Preparation of 2-(2H-1,2,3-benzotriazol-2-yl)-4-methyl-6-(2-methylprop-2-enyl)phenol in Benzyl Alcohol Alone 2-(2-Hydroxy-5-methylphenyl)benzotriazole (45 g; 0.1997 mol) is charged under nitrogen into a reactor with potassium carbonate (30.33 g; 0.2171 mol) and 45 ml of benzyl alcohol. The medium is heated to 80-85° C. A solution of catalyst prepared beforehand by mixing with stirring tributylamine (9.25 g; 49.9 mmol) and methallyl chloride (36.16 g; 0.3994 mol) is poured into the medium. After addition, the medium is heated at 80-85° C. for 19 hours. After reaction, the medium is cooled and diluted with water (45 ml). The organic phase is washed so with water (twice 45 ml). After separation of the phases by settling, the medium is concentrated under vacuum to remove the water. The medium is rediluted with 15 ml of benzyl alcohol and is then heated to 200-206° C. After reaction, the medium is cooled and concentrated under vacuum. 103 ml of isopropanol are then added at 80° C. The medium is then cooled to a temperature of between 0 and 10° C. The solid is filtered off and washed with isopropanol. After drying under vacuum, 46.3 g of white crystals are obtained (83% yield and 99.5% purity).

EXAMPLE 4

Preparation of 2-(2H-1,2,3-benzotriazol-2-yl)-4-methyl-6-(2-methylprop-2-enyl)phenol in a Tetralin/Water Two-Phase Mixture 2-(2-Hydroxy-5-methylphenyl)benzotriazole (15 g; 65.6 mmol) is charged under nitrogen into a reactor with potassium carbonate (10.11 g; 72.4 mmol), tetrabutylammonium chloride (0.91 g; 3.28 mmol) and 45 ml of a water/tetralin mixture (2/1). The medium is heated to 80-85° C. and methallyl chloride (10.25 g; 0.112 mol) is added dropwise. After addition, the medium is heated at 80-85° C. After 26 hours, the medium is cooled and the phases are separated by settling. The organic phase is washed with 35 ml of water. After separation of the phases by settling, the medium is concentrated under vacuum to remove the water. The medium is rediluted with 12 ml of tetralin and is then heated at 200-206° C. The medium is cooled and concentrated under vacuum. 30 ml of isopropanol are then added at 80° C. The medium is then cooled to a temperature of between 0 and 10° C. The solid is filtered off and washed with isopropanol. After drying under vacuum, 15.8 g of white crystals are obtained (85% yield and 99.7% purity).

EXAMPLE 5

Preparation of 2-(2H-1,2,3-benzotriazol-2-yl)-4-methyl-6-(2-methylprop-2-enyl)phenol in Water and Diphenyl Ether 2-(2-Hydroxy-5-methylphenyl)benzotriazole (45 g; 0.1997 mol), potassium carbonate (30.40 g; 0.22 mol), tributylammonium chloride (2.77 g; 10 mmol) and 90 ml of water are introduced into a reactor under nitrogen. The medium is heated to 80-85° C. Next, methallyl chloride (23.79 g; 0.26 mol) is added dropwise. After addition, the medium is maintained at 80-85° C. until conversion is complete. After reaction, the medium is cooled and diluted with a diphenyl ether/water mixture (1/1) (90 ml). The phases of the medium are separated by settling and the organic phase is washed with water (100 ml). The aqueous phase is separated out and the organic phase is placed under vacuum to remove the water. The medium is rediluted in 20 ml of solvent and is heated to 200-206° C. After reaction, the medium is cooled and the solvent is removed by distillation. 104 g of isopropanol are then added at 80° C. and the medium is then cooled to between 0 and 10° C. The precipitate is filtered off and washed with isopropanol (twice 11.3 ml). The product is dried under vacuum and 51.2 g (92.5% yield) of white crystals are obtained in a purity of 99.8%.

The invention claimed is:

1. A process for preparing a 2-hydroxyphenyl alkenyl benzotriazole compound, the process comprising:
   1) reacting a 2-hydroxyphenylbenzotriazole compound in water, at least one organic solvent with a boiling point of greater than 200° C., or both, with an alkenyl halide in the presence of at least one phase-transfer agent and at least one base to obtain a 2-O-alkenylphenylbenzotriazole compound; and
   2) heating a reaction mixture comprising the 2-O-alkenylphenylbenzotriazole compound and at least one organic solvent with a boiling point of greater than 200° C. to a temperature above 170° C. to form a 2-hydroxyphenyl alkenyl benzotriazole compound.

2. The process according to claim 1, comprising:
   i) the reacting 1) to obtain the 2-O-alkenylphenylbenzotriazole;
   ii) cooling the reaction mixture comprising the 2-O-alkenylphenylbenzotriazole compound to room temperature and optionally diluting a resulting reaction medium with water, the organic solvent with a boiling point of greater than 200° C., or both;
   iii) removing water from the reaction medium;

iv) heating a resulting reaction mixture comprising the 2-O-alkenylphenylbenzotriazole compound to a temperature of greater than 170° C. in the presence of at least one organic solvent with a boiling point of greater than 200° C. to form a 2-hydroxylphenyl alkenyl benzotriazole compound;

v) removing at least one solvent from the 2-hydroxyphenyl alkenyl benzotriazole compound; and vi) recrystallizing the 2-hydroxyphenyl alkenyl benzotriazole compound in the presence of at least one recrystallization solvent.

3. The process according to claim 1, which occurs in a single reactor.

4. The process according to claim 1, wherein:
a 2-hydroxyphenyl alkenyl benzotriazole compound of formula (1) below is prepared:

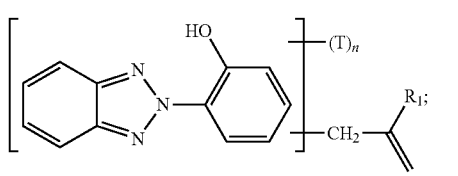
(1)

n represents an integer between 0 and 3 inclusive;

T independently represents a linear or branched $C_1$-$C_8$ alkyl radical, a halogen, or a linear or branched $C_1$-$C_4$ alkoxy radical;

$R_1$ represents hydrogen or a methyl radical; and the process comprises:

1) reacting a compound of formula (5):

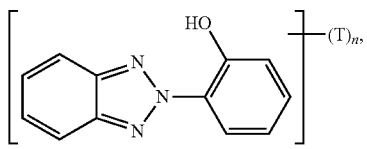
(5)

in the water, the at least one organic solvent with a boiling point of greater than 200° C., or both, in the presence of the at least one phase-transfer agent and the at least one base, with an alkenyl halide of formula (6):

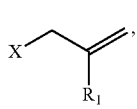
(6)

wherein X represents a halogen atom, and $R_1$ represents hydrogen or methyl, to obtain a compound of formula (7):

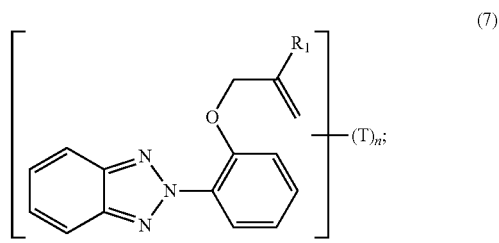
(7)

and (2) heating a reaction mixture comprising the compound of formula (7) to a temperature of greater than 170° C. in the presence of at least one organic solvent with a boiling point of greater than 200° C.

5. The process according to claim 1, wherein the organic solvent is a water-immiscible solvent having a boiling point of greater than 200° C.

6. The process according to claim 1, wherein:
a temperature of the reaction mixture during the reacting 1) is between 20° C. and 150° C.; and
a temperature of the reaction mixture during the heating 2) is between 170° C. and 250° C.

7. The process according to claim 1, wherein the 2-hydroxyphenylbenzotriazole compound is selected from the group consisting of 2-(2-hydroxy-5-methylphenyl)benzotriazole, 2-(2-hydroxy-5-tert-octylphenyl)benzotriazole and 2-(2'-hydroxy-5'-methylphenyl)-5-chlorobenzotriazole.

8. The process according to claim 1, wherein the alkenyl halide is selected from the group consisting of 1-chloro-2-propene, 1-bromo-2-propene, 1-chloro-2-methyl-2-propene and 1-bromo-2-methyl-2-propene.

9. The process according to claim 1, wherein, in the reacting 1):
the alkenyl halide is present in a ratio ranging from 1.05 to 1.7 equivalents relative to the 2-hydroxyphenylbenzotriazole compound; and
a concentration of the 2-hydroxyphenylbenzotriazole compound ranges from 5% to 80% by weight relative to the total weight of the reaction medium.

10. The process according to claim 1, wherein the phase-transfer agent is at least one selected from the group consisting of a tetrabutylammonium halide, tetrabutylammonium hydrogenosulfate, benzyltrimethyl-ammonium chloride and a preformed catalyst formed by reacting tributylamine with an alkenyl halide.

11. The process according to claim 1, wherein the at least one phase-transfer agent is present in a ratio ranging from 3 mol % to 15 mol % relative to the 2-hydroxyphenylbenzotriazole compound.

12. The process according to claim 1, wherein the base is an alkaline-earth metal base.

13. Process according to claim 1, wherein the at least one base is present in a ratio ranging from 0.7 to 1.5 equivalents relative to the 2-hydroxyphenylbenzotriazole compound.

14. The process according to claim 1, wherein the organic solvent is at least one selected from the group consisting of benzyl alcohol, diethylene glycol monobutyl ether, diphenyl ether, tetralin, methylnaphthalene and a biphenyl/diphenyl ether mixture.

15. The process according to claim 2, wherein the recrystallization solvent is selected from the group consisting of isopropanol, methanol, ethanol, benzyl alcohol, and mixtures thereof.

16. A process for preparing a siloxane compound containing a benzotriazole, the process comprising hydrosilylating the 2-hydroxyalkenylphenylbenzotriazole compound prepared according to claim 1 in the presence of a catalyst and of a solvent with a siloxane comprising an SiH function.

17. The process according to claim 16, wherein:

the siloxane compound is represented by formula (4):

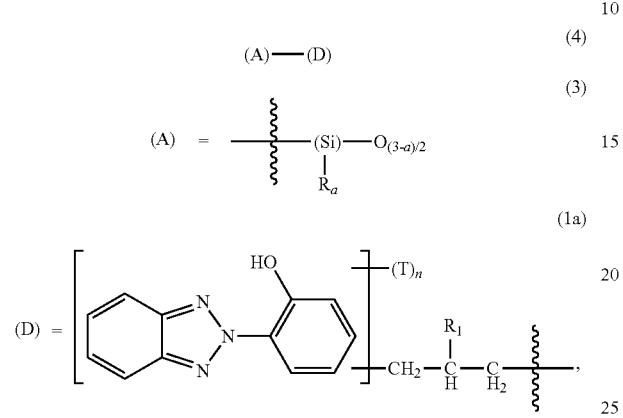

wherein:

R independently represents a linear or branched and optionally halogenated or unsaturated $C_1$-$C_{30}$ alkyl radical, a $C_6$-$C_{12}$ aryl radical, a linear or branched $C_1$-$C_{10}$ alkoxy radical or a group —OSi(CH$_3$)$_3$;

a represents an integer between 0 and 2 inclusive;

n represents an integer between 0 and 3 inclusive;

T independently represents a linear or branched $C_1$-$C_8$ alkyl radical, a halogen, or a linear or branched $C_1$-$C_4$ alkoxy radical;

$R_1$ represents hydrogen or a methyl radical;

the siloxane compound of formula (4) optionally further comprises at least one unit of formula:

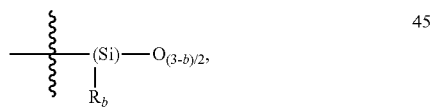

wherein b represents 1, 2 or 3; and the process comprises at least hydrosilylating a 2-hydroxyalkenylphenylbenzotriazole compound of formula (1):

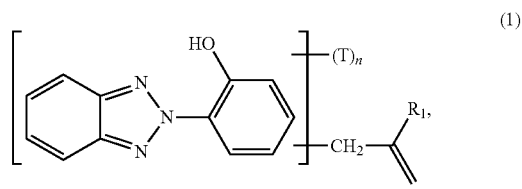

with a siloxane of formula (2):

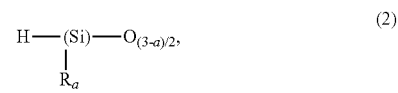

in the presence of the catalyst and the solvent.

18. The process according to claim 17, wherein:

the compound Drometrizole Trisiloxane corresponding to formula (C):

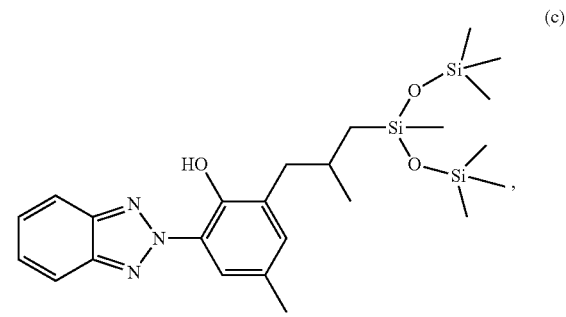 [SMILES: Cc1cc(CC(C)C[Si](C)(O[Si](C)(C)C)O[Si](C)(C)C)c(O)c(-n2nc3ccccc3n2)c1]

is prepared; and the process comprises at least hydrosilylating the compound 2-(2H-1,2,3-benzotriazol-2-yl)-4-methyl-6-(2-methylprop-2-enyl)phenol which is obtained by the process according to claim 4 with the siloxane 1,1,1,3,5,5,5-heptamethyltrisiloxane in the presence of a the catalyst and a the solvent.

* * * * *